United States Patent
Rothermel et al.

(10) Patent No.: US 8,439,031 B1
(45) Date of Patent: May 14, 2013

(54) PATIENT TREATMENT SYSTEM WITH A PATIENT INTERFACE MOUNTED CONTROL

(75) Inventors: Justin Rothermel, Pittsburgh, PA (US); J. Raymond Pujol, Murrysville, PA (US); Robert G. Rybicki, Pittsburgh, PA (US)

(73) Assignee: Ric Investments, LLC, Wilmington, DE (US)

( * ) Notice: Subject to any disclaimer, the term of this patent is extended or adjusted under 35 U.S.C. 154(b) by 1242 days.

(21) Appl. No.: 11/481,291

(22) Filed: Jul. 5, 2006

Related U.S. Application Data

(60) Provisional application No. 60/697,141, filed on Jul. 7, 2005.

(51) Int. Cl.
- *A61M 16/00* (2006.01)
- *A61M 16/06* (2006.01)
- *A62B 18/02* (2006.01)
- *A62B 18/08* (2006.01)

(52) U.S. Cl.
USPC ............ 128/204.21; 128/205.25; 128/207.11; 128/204.18; 128/206.21

(58) Field of Classification Search ............ 128/204.18, 128/204.21, 204.24, 205.11, 205.25, 206.16, 128/206.21, 207.12, 206.28
See application file for complete search history.

(56) References Cited

U.S. PATENT DOCUMENTS

| | | | | |
|---|---|---|---|---|
| 4,651,728 A * | 3/1987 | Gupta et al. | ............. | 128/201.28 |
| 5,117,819 A * | 6/1992 | Servidio et al. | .......... | 128/204.18 |
| 5,685,296 A | 11/1997 | Zdrojkowski et al. | | |
| 5,694,923 A | 12/1997 | Hete et al. | | |
| 5,913,307 A * | 6/1999 | Taieb et al. | ............. | 128/205.23 |
| 5,937,855 A | 8/1999 | Zdrojkowski et al. | | |
| 5,970,975 A | 10/1999 | Estes et al. | | |
| 6,017,315 A | 1/2000 | Starr et al. | | |
| 6,240,921 B1 * | 6/2001 | Brydon et al. | ........... | 128/205.23 |
| 6,629,527 B1 * | 10/2003 | Estes et al. | ............. | 128/204.18 |
| 2003/0029451 A1 * | 2/2003 | Blair et al. | ............. | 128/204.18 |
| 2004/0087866 A1 * | 5/2004 | Bowman et al. | ............. | 600/529 |
| 2004/0163648 A1 * | 8/2004 | Burton | ..................... | 128/204.21 |
| 2006/0048782 A1 * | 3/2006 | Gossweiler | ............. | 128/205.12 |
| 2006/0096596 A1 * | 5/2006 | Occhialini et al. | ........ | 128/204.18 |

* cited by examiner

*Primary Examiner* — Justine Yu
*Assistant Examiner* — Valerie L Skorupa
(74) *Attorney, Agent, or Firm* — Michael W. Haas

(57) ABSTRACT

A patient treatment system that comprises a gas delivery system, a patient interface, and a control interface to provide a pressurized flow of breathable gas. The patient interface is in communication with the gas delivery system, and is constructed to interface with a patient to provide the breathable gas to the patient. The control interface is carried by the patient interface, and enables the patient to control at least one aspect of the patient treatment system.

18 Claims, 6 Drawing Sheets

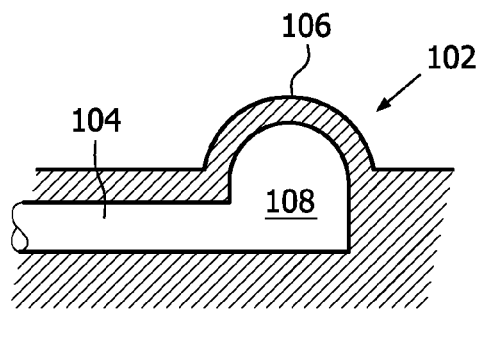
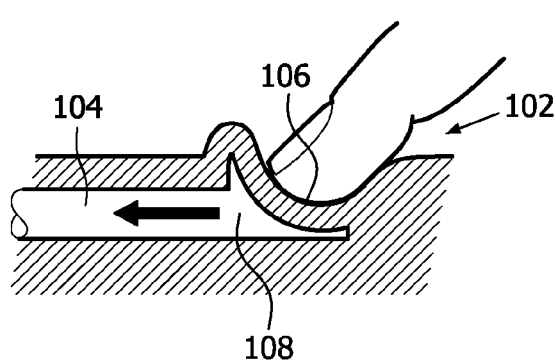
FIG. 11A    FIG. 11B
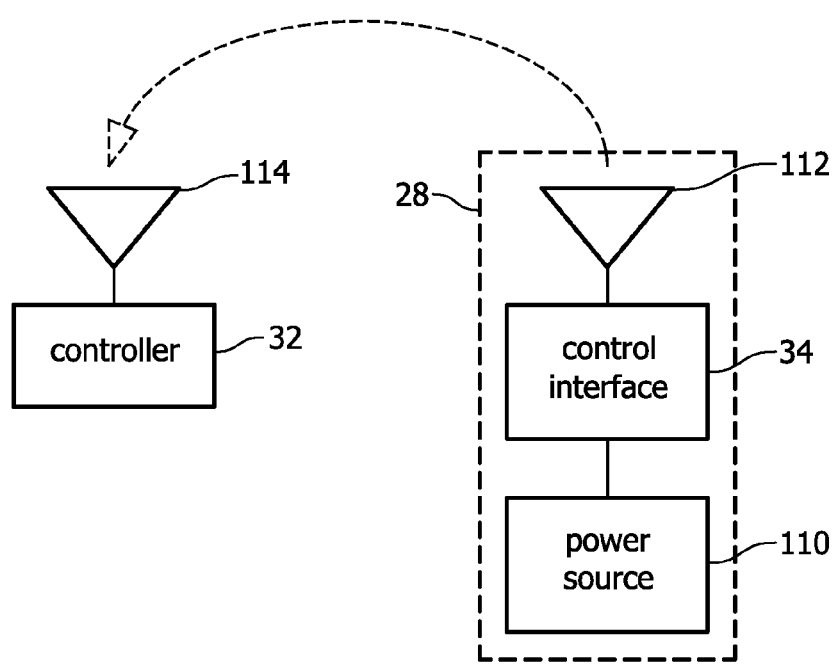
FIG. 12

PATIENT TREATMENT SYSTEM WITH A PATIENT INTERFACE MOUNTED CONTROL

CROSS-REFERENCE TO RELATED APPLICATIONS

This application claims priority under 35 U.S.C. §119(e) from provisional U.S. patent application No. 60/697,141, filed Jul. 7, 2005 the contents of which are incorporated herein by reference.

BACKGROUND OF THE INVENTION

1. Field of the Invention

The invention relates to the treatment of sleep disordered breathing.

2. Description of the Related Art

Patients that suffer from sleep disordered breathing are typically treated with a Positive Airway Pressure (PAP) apparatus that provides a pressurized flow of breathing gas according to a predetermined mode of ventilation, such as continuous positive airway pressure, bi-level positive airway pressure, proportional positive airway pressure, and proportional assist ventilation, among others. The pressurized gas supports a patient's airway as the patient sleeps such that episodes of cessation of breathing that are associated with sleep disordered breathing are avoided, or during episodes associated other respiratory ailments.

Conventional PAP apparatuses generally enable the patient to control various aspects of operation of the apparatus related to the flow of breathing gas delivered by the apparatus during operation. For example, the patient may control a ramp setting, a pressure relief setting (i.e., C-Flex™), a humidifier setting, a temperature setting, an oxygen concentration level setting, an on/off control, or other settings or controls. However, the patient is usually required to input these settings and controls at an input module located on the portion of the apparatus that generates the flow of gas. This portion of the apparatus is generally a substantial piece of equipment that is not usually kept in bed with the patient during use. Consequently, to adjust one or more aspects of operation of the apparatus while in use (e.g., at night while the patient is sleeping), the patient, or another individual, must go to the portion of the apparatus that generates the flow of gas, locate the input module, and select the desired settings and/or controls. This makes the adjustment of the apparatus during use inconvenient and inefficient for the patient.

U.S. Pat. No. 5,970,975 to Estes et al. discloses that a remote control may be used by the patient to adjust one or more aspects of operation of a PAP apparatus. However, making adjustments with a remote control would still require the patient to locate the remote control, which may not be a trivial task due to the fatigue or sleepiness of the patient and/or the darkness of the room in which the patient is sleeping. Further, the remote control disclosed in the Estes patent may be subject to misplacement and loss by the patient.

SUMMARY OF THE INVENTION

The invention relates to a patient treatment system that provides a pressurized flow of breathable gas. The patient treatment system comprises a gas delivery system, a patient interface, and a control interface. The patient interface is in communication with the gas delivery system, and is constructed to interface with a patient to provide the breathable gas to the patient. The control interface is carried by the patient interface, and enables the patient to control at least one aspect of the patient treatment system.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 11A and 11B illustrate a switch according to an alternative embodiment.

FIG. 12 is a schematic representation of an alternative configuration of the control interface, in accordance with an embodiment of the invention.

DETAILED DESCRIPTION OF THE EXEMPLARY EMBODIMENTS

Figure 1:
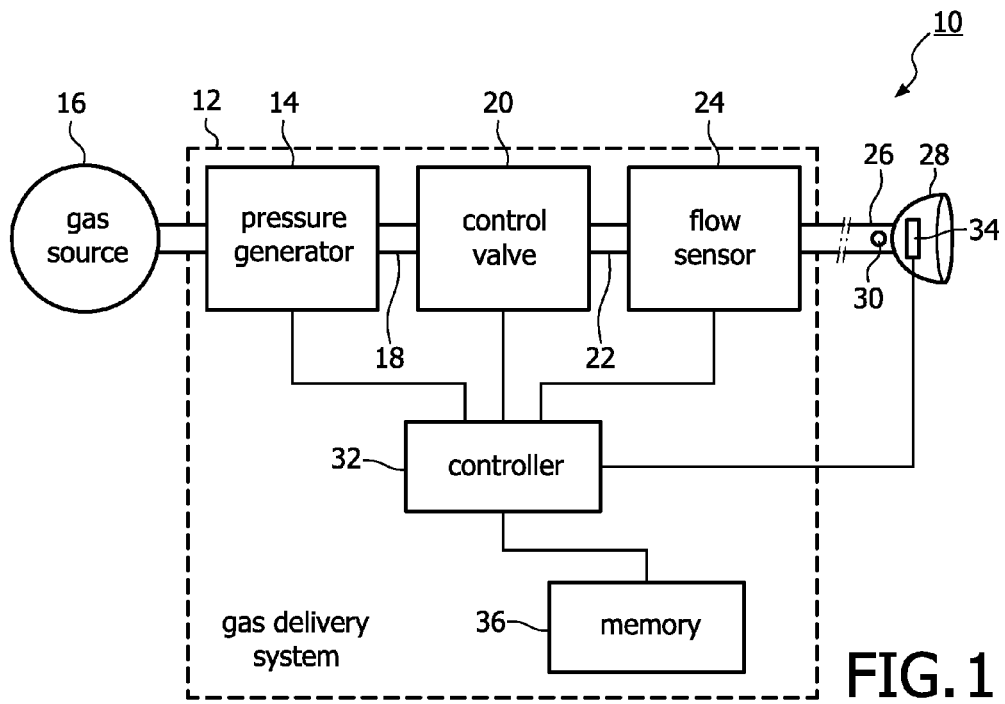
FIG. 1 is a schematic representation of a patient treatment system, according to an embodiment of the invention.

FIG. 1 schematically illustrates an exemplary first embodiment of a patient treatment system 10 according to the present invention. The system 10 is capable of providing and automatically controlling the pressure of breathing gas delivered to a patient using a predetermined mode of ventilation. Patient treatment system 10 includes a gas delivery system 12 that controls a flow of breathing gas to a patient. Gas delivery system 12 includes a pressure generator 14 that receives a supply of breathable gas from a breathable gas source 16 and elevates the pressure of that gas for delivery to the airway of a patient. Pressure generator 14 is any device, such as a blower, compressor (scroll, screw, piston), or bellows that is capable of elevating the pressure of the received breathing gas for delivery to a patient. The present invention also contemplates that the pressure generator 14 can be defined by a canister or tank of pressurized gas, with the pressure delivered to the patient being controlled by a pressure regulator. Thus, while the embodiment of FIG. 1 illustrates a separate gas source 16, the present invention contemplates that the gas source can be considered to be part of the gas delivery system 12. In addition, in another embodiment, the gas source 16 can be provided in the same housing as the rest of the gas delivery system 12. In yet another embodiment, the gas source is not only considered part of the gas delivery system 12, but also provides the pressurized flow of breathable gas in a manner that can eliminate the separate pressure generator 12. The invention also contemplates embodiments in which the breathable gas from gas source 16 is delivered with supplemental oxygen from an oxygen source to elevate the level of oxygen concentration in the gas delivered to the patient. This may include mixing the breathable gas from gas source 16 with the supplemental oxygen at gas delivery system 12, or downstream from gas delivery system 12.

In one embodiment of the present invention, pressure generator 14 is a blower that is driven at a constant speed during the course of the pressure support treatment to produce a constant pressure or flow rate at its output 18. The present invention contemplates that breathing gas source 16 is any supply of breathing gas, such as ambient atmosphere, a tank of pressurized gas, and an oxygen concentrator. Furthermore, the breathing gas for delivery to the patient can be any gas, such as air or an oxygen mixture, e.g., heliox, or a mixture of a breathing gas and a medication, which can be in gaseous form, such as nitric oxide, or nebulized.

In the illustrated embodiment, gas delivery system 12 includes a control valve 20. The breathable gas is delivered from pressure generator 14 to control valve 20 downstream of the pressure generator 14, at an elevated pressure. Control valve 20, either alone or in combination with pressure generator 14, controls the final pressure of gas at exit 22 exiting the pressure/flow generating system, which, in this embodiment includes pressure generator 14 and control valve 20. Examples of a suitable pressure/flow controller include at least one valve, such as sleeve or poppet valve, that exhausts gas from the patient circuit as a method of controlling the pressure in the patient circuit. U.S. Pat. No. 5,694,923 to Hete et al., the contents of which are incorporated herein by reference, teaches a dual poppet valve system suitable for use as control valve 20 that exhausts gas to atmosphere and restricts the flow of gas from the pressure generator 14 to the patient. Other suitable pressure/flow controllers are believed to be well known to those skilled in the art.

In embodiments in which pressure generator 14 is a blower that operates at all times at only one speed, then control valve 20 alone can be used to control the final pressure and flow rate for the breathing delivered to the patient. However, the present invention also contemplates controlling the operating speed of pressure generator 14 in combination with control valve 20 to control the final pressure and flow rate for the breathing gas delivered to the patient. For example, a pressure or flow rate close to the desired pressure or flow rate can be set by establishing an appropriate operating speed for pressure generator 14 along with control valve 20 so that the two, operating together, determine the final pressure for the breathing gas delivered to the patient.

In the embodiment of FIG. 1, gas delivery system 12 includes a sensor 24. The flow of breathing gas output from exit 22 of control valve 20 is delivered to sensor 24 to determine the instantaneous volume (V) of gas delivered to the patient, the instantaneous flow rate (V') of such gas to the patient, or both. Sensor 24 is any device suitable for measuring these parameters, such as a spirometer, pneumotach, variable orifice transducer, a differential pressure transducer, or other conventional flow transducer. In the illustrated embodiment, sensor 24 is provided at a location relatively distant from patient interface assembly 28, as will be described. For example, U.S. Pat. No. 6,017,315 to Starr et al., the contents of which are incorporated herein by reference, teaches a quantitative flow member that is located at the patient interface assembly 28. The present invention also contemplates, however, locating sensor 24 at any location along a patient circuit 26, as will also be described.

The flow of breathing gas is carried from gas delivery system 12 to the patient via patient circuit 26, which is typically a single flexible conduit that carries the flow of breathing gas to a patient interface assembly 28. Patient interface assembly 28 includes patient interface appliance 48 (e.g., see FIG. 3), either invasive or non-invasive, such as a nasal mask, nasal/oral mask, total face mask, nasal cannula, endotracheal tube, or tracheal tube, suitable for communicating a supply of breathing gas to the airway of a patient. The patient interface assembly 28 may also include headgear assembly 50, such as mounting straps or a harness, and/or a proximate portion of the patient circuit 26, as will be described later. In the illustrated embodiment, the patient interface assembly 28 and/or patient circuit 26 includes a suitable exhaust port 30 for exhausting gas from these components to ambient atmosphere. Exhaust port 30 is preferably a passive exhaust port in the form of a continuously open port that imposes a flow restriction on the exhaust gas to permit control of the pressure of gas within patient interface assembly 28. It is to be understood, however, that exhaust port 30 can be an active exhaust port that assumes different configurations to control the exhaust rate. Examples of suitable exhaust ports are taught, for example, in U.S. Pat. Nos. 5,685,296 and 5,937,855 both to Zdrojkowski et al.

As shown, gas delivery system 12 includes an electronic controller 32 that controls the various operating aspects of gas delivery system 12. For example, the output of sensor 24 is provided to controller 32 for processing, if needed, to determine the instantaneous volume (V) of gas delivered to the patient, the instantaneous flow rate (V') of such gas to the patient, or both. In some embodiments, the controller 32 determines the instantaneous volume by integrating the measured flow rate. Because in one embodiment the flow sensor 24 may be located relatively far from the patient interface assembly 28, in order to determine the actual flow rate of gas to the patient or the actuation flow rate of gas from the patient, which is considered a negative flow, controller 32 receives the output from sensor 24 as an estimated flow. The control unit 32 processes this estimated flow information, for example, by performing leak estimation, to determine the actual flow at the patient's airway, as is known to those skilled in the art.

A control interface 34 provides data and commands to controller 32 of gas delivery system 12. Control interface 34, which is discussed with greater particularity below, may include any device suitable to provide information and/or commands to controller 32 via a hardwire or wireless connection. Typical examples of control interface 34 may include a keypad, keyboard, touch pad, mouse, microphone, switches, button, dials, or any other devices that allow a user to input information to the treatment system 10.

The present invention contemplates that in an embodiment (not illustrated), the patient circuit 26 can be a two-limb circuit, which is common in conventional ventilators. In a two-limb circuit, the first limb, like patient circuit 26, delivers breathing gas to the patient, except that it lacks an exhaust port. Instead, the second limb carries the exhaust gases from the patient to ambient atmosphere. Typically, an active exhaust port in the second limb under the control of a controller (e.g. controller 32) provides the desired level of positive end expiratory pressure (PEEP) to the patient. In addition, gas delivery system 12 and related components can include other conventional devices and components, such as a humidifier, heater, bacteria filter, temperature sensor, pressure sensor, flow sensor, humidity sensor, and a gas sensor (e.g., a capnometer), that filter, measure, monitor, and analyze the flow of gas to or from the patient.

Controller 32 controls the actuation of control valve 20, thereby controlling the pressure of the breathing gas delivered to the patient. In one embodiment, controller 32 comprises a processor that is suitably programmed with the necessary algorithm or algorithms for calculating the pressure to be applied to the patient according to various modes of ventilation. In a more advanced embodiment of the present invention, the gas delivery system 12 includes a memory 36 associated with controller 32 for storing the programming necessary to perform any of a plurality of modes of ventilation, depending on which mode of ventilation is selected by the caregiver or patient using control interface 34. Memory 36 may also be capable of storing data regarding the operation of the patient treatment system 10, input commands, alarm thresholds, as well as any other information pertinent to the operation of the patient treatment system 10, such as measured values of gas flow, volume, pressure, device usage, operating temperatures, and motor speed.

Figure 2:
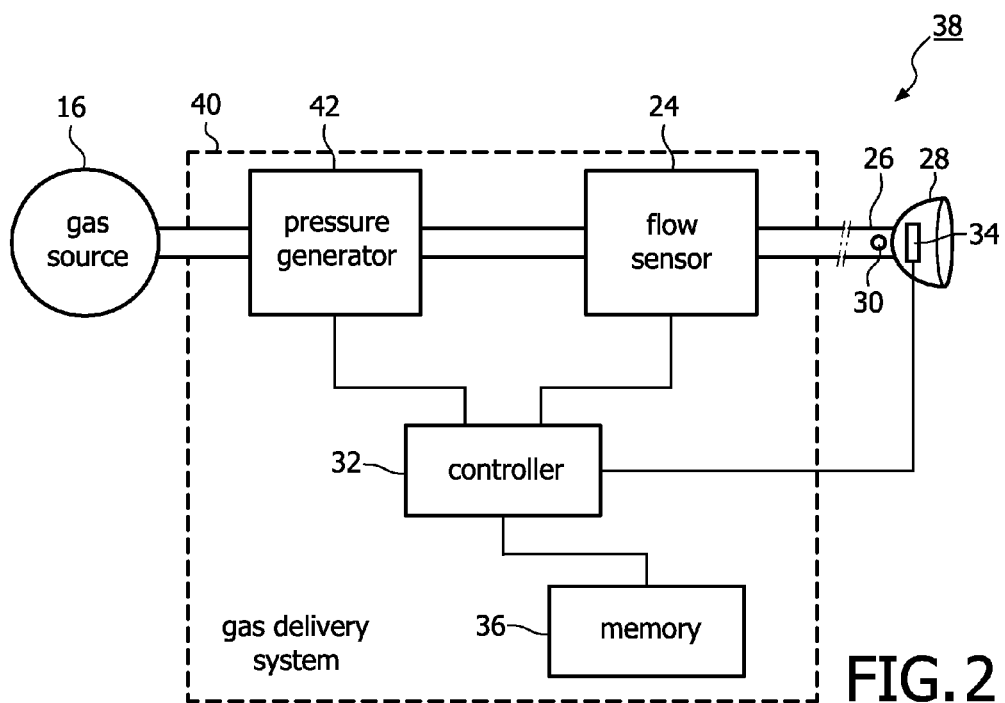
FIG. 2 is a schematic representation of an alternative patient treatment system, according to an embodiment of the invention.

An alternative embodiment of a patient treatment system 38, including a gas delivery system 40, is discussed below with reference to FIG. 2. Unlike patient treatment system 10 of FIG. 1, the final pressure of the breathing gas delivered to the patient is not controlled by the control valve, either alone or in combination with the pressure generator 14. Rather, gas delivery system 40 shown in FIG. 2 controls the pressure of breathing gas delivered to the patient based only on the output of a pressure generator 42. That is, controller 32 controls the pressure of breathing gas delivered to the patient by controlling the motor speed of pressure generator 42. In one embodiment, pressure generator 42 is a blower. The present invention contemplates providing, if necessary, ancillary feedback systems, such a pressure monitor in patient circuit 26, a speed monitor for the blower motor, or a pressure generator output monitor that provides feedback data to controller 32 for controlling the operation of pressure generator 42.

FIGS. 3-6 illustrate several configurations of control interface 34, in accordance with several embodiments of the present invention. More particularly, control interface 34 is shown as being provided on patient interface assembly 28. For the purposes of this disclosure, the "patient interface assembly" 28 on which the control interface 34 may be provided, is defined as including the patient interface appliance 48, the headgear assembly 50, such as one or more straps or a harness that may optionally be provided for mounting patient interface appliance 48 on the patient, a proximate portion 52 of the patient circuit 26, and/or any structure that is mounted or connected to such patient interface appliance 48, headgear assembly 50, or proximate portion 52, and is immediately accessible (within reach) of the patient. The patient interface appliance 48 may include any appliance, either invasive or non-invasive, such as a nasal mask, nasal/oral mask, total face mask, nasal cannula, endotracheal tube, or tracheal tube, suitable for communicating a supply of breathing gas to the airway of a patient. It should be appreciated that in some embodiments, the headgear assembly 50 need not be provided and the patient interface appliance 48 can be otherwise contoured to be secured to the patient. Alternatively, an adhesive can be used to adhere patient interface appliance 48 to the patient. The proximity or location of control interface 34 in relation to the patient enhances the patients ability to control the flow of breathing gas generated by gas delivery system 12. For example, in the embodiments illustrated (and in other embodiments incorporating control interface 34 into a patient interface and/or patient circuit) the control interface 34 is readily accessible to the patient during use. This enables the patient to easily locate control interface 34 and adjust the flow of gas with a reduced amount of effort. Further, since control interface 34 is carried on patient interface assembly 28, drawbacks associated with the misplacement or loss of a separate remote control device are avoided.

Figure 3:
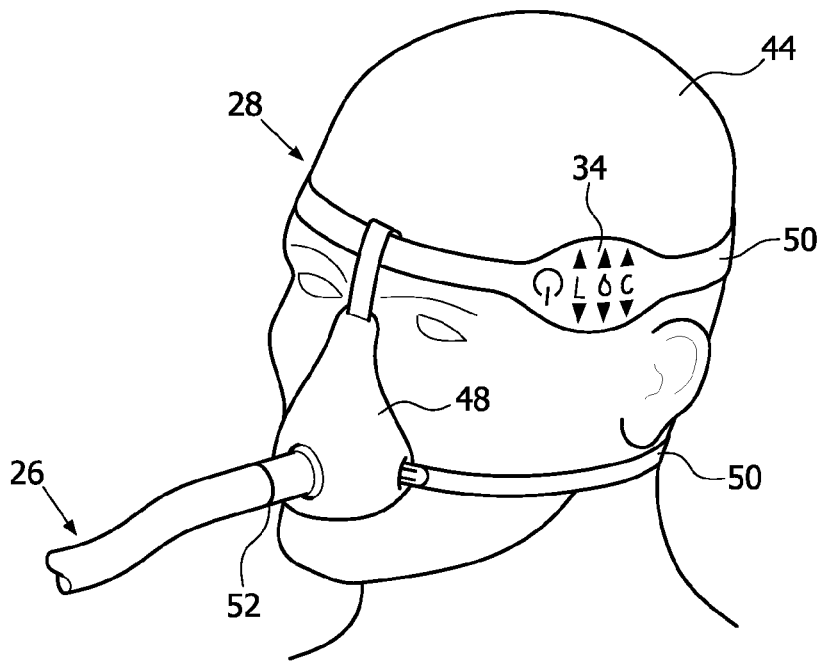
FIG. 3 is an exemplary illustration of a control interface provided on a patient interface assembly, in accordance with an embodiment of the invention.

FIG. 3 illustrates an embodiment of control interface 34 mounted on patient interface assembly 28. Patient interface assembly 28 is depicted as being mounted on a patient 44 such that patient 44 receives the flow of breathing gas from gas delivery system 12 via patient circuit 26. As shown, patient interface assembly 28 includes a patient interface appliance 48 that rests over the patient's nose and/or mouth to deliver the gas, headgear assembly 50 that hold patient interface appliance 48 in place. Control interface 34 is illustrated in FIG. 3 as being integrally provided on the headgear assembly 50.

Figure 4:
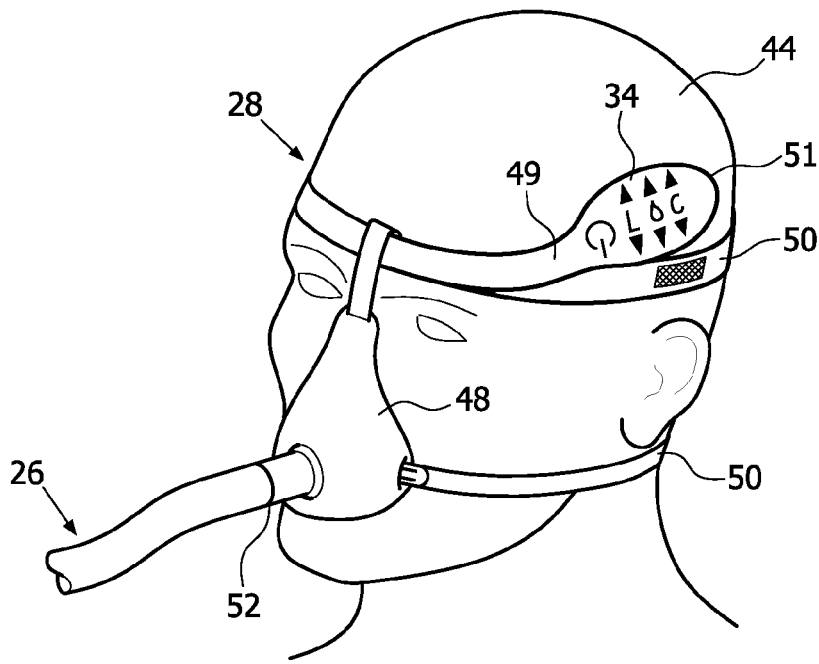
FIG. 4 is an exemplary illustration of the control interface provided on the patient interface assembly, according to an embodiment of the invention.

FIG. 4 illustrates control interface 34 provided on patient interface assembly 28 such that patient 44 may view the controls, in accordance with an embodiment of the invention. As shown, headgear assembly 50 includes a tethered leash portion 49 with a free end 51. The control interface 34 is provided on the free end 51 of the leash portion 49 so that patient 44 can manually hold control interface 34 in his/her view while inputting control settings via control interface 34. When control interface 34 is not in use, free end 51 may be removably attached to headgear assembly 50 so that leash portion 49 and control interface 34 will not interfere with the comfort of patient 44. For example, headgear assembly 50 and free end 51 may be removably attached via a hook and loop fastener (e.g., Velcro® fastener), or another mechanism for removably attaching two members. In an alternative embodiment, leash portion 49 may be permanently fixed at both ends to headgear assembly 50, but still provide enough slack to enable the patient 44 to view control interface 34. In another embodiment, the control interface 34 includes a wireless transmitter that is removably connected to the patient interface assembly 28 by a detachable connection, such as a Velcro® fastener strip.

Figure 5:
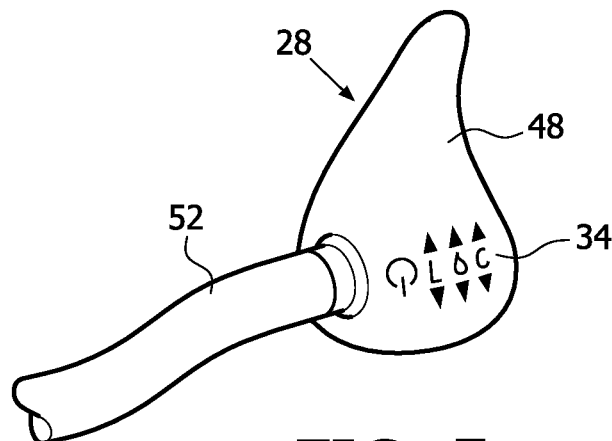
FIG. 5 illustrates the control interface provided on the patient interface assembly according to an embodiment of the invention.
Figure 6:
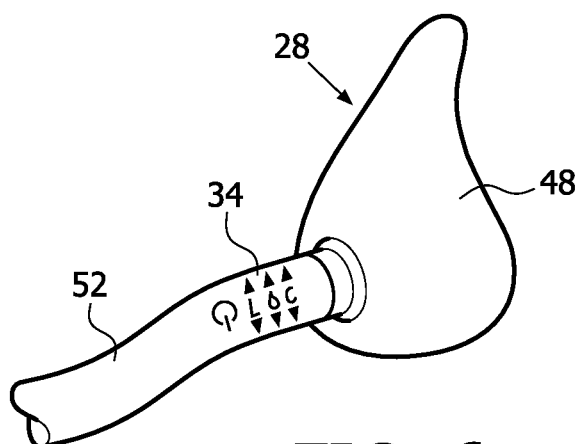
FIG. 6 is an exemplary illustration of the control interface provided on a patient circuit, in accordance with an embodiment of the invention.

FIG. 5 illustrates an embodiment of control interface 34 provided on patient interface assembly 28 at patient interface appliance 48. FIG. 6 illustrates an embodiment of control interface 34 provided on patient interface assembly 28 at proximate portion 52 of patient circuit 26. In either embodiment, patient interface appliance 48 may be held in place on a patient by, for example, one or more straps (not shown), or by another harness structure that keeps patient interface appliance 48 in position with respect to the patient during the delivery of a flow of pressurized breathing gas. Control interface 34 may include an exterior configuration that is formed integrally with patient interface appliance 48, headgear assembly 50, or proximate portion 52, or may be formed separately and mounted thereon.

In FIGS. 3-6, the patient may adjust one or more aspects of operation of the patient treatment system 10 by manipulating control interface 34. By manipulating control interface 34, patient 44 may adjust, for example, a humidifier setting, a pressure relief setting, a ramp setting, an oxygen concentration level setting, and/or an on/off control. It will be appreciated that this is not a comprehensive list of the aspects of operation of gas delivery system 12 and/or patient treatment system 10, and that more or less control may be provided to patient 44 at control interface 34. Although control interface 34 is illustrated as including one or more manually depressible buttons 52, in other embodiments control interface 34 may include a variety of mechanisms that would enable patient 44 to adjust one or more aspects of operation of patient treatment system 10. For example, control interface 34 may include a knob, a switch, a lever, or other input mechanisms.

In one embodiment, not shown in FIGS. 3-6, control interface 34 includes one or more devices suitable to provide information related to patient treatment system 10 to an individual (e.g., a patient, a caregiver, etc.) such as, a screen, a printer, one or more indicator light, a speaker, or other devices that enable the provision information to the individual. For example, control interface 34 may include an liquid crystal display (LCD) screen that provides information to an individual.

In some embodiments, control interface 34 may be the only mechanism to enable adjustment of patient treatment system 10. However, in other embodiments, an additional or supplemental input module may be provided. The other input module may include, for example, an input module provided to the patient, or another user (e.g. a caregiver) at gas delivery system 12, or elsewhere on system 10. The additional input module may also be a remote control device.

Figure 7:
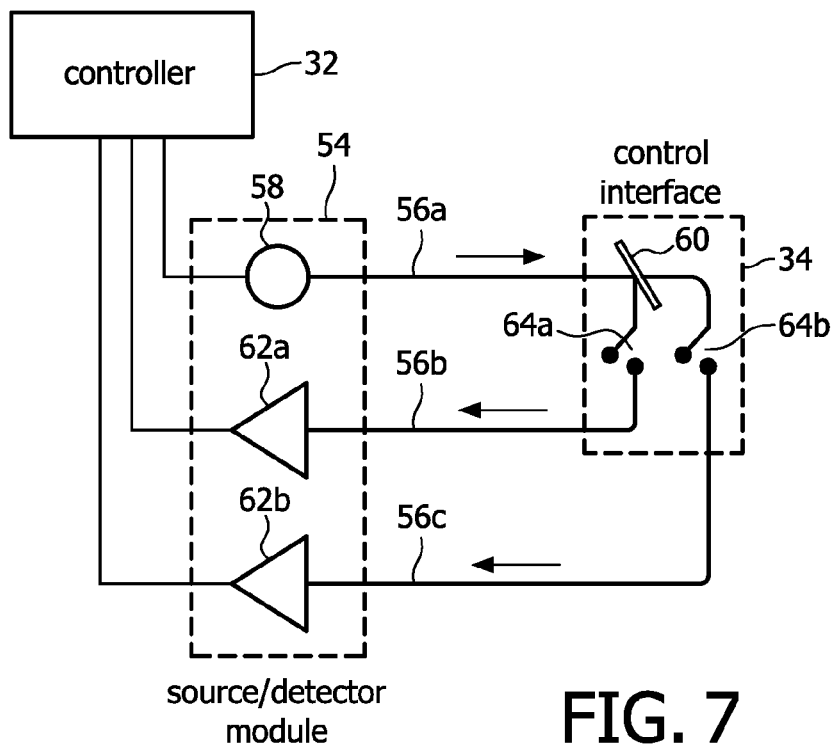
FIG. 7 is a schematic representation of the control interface, according to an embodiment of the invention.

FIG. 7 illustrates an embodiment in which control interface 34 passively interacts with a remotely generated non-electronic signal to enable the patient (or another user) to control gas delivery system 12. Implementing an embodiment of control interface 34 that uses only passive interaction with a non-electronic signal may be advantageous because electronic signals may be undesirable for certain applications or environments.

In the embodiment shown in FIG. 7, control interface 34 is operatively linked to a source/detector module 54 associated with gas delivery system 12. Source/detector module 54 is provided remote from control interface 34 at gas delivery system 12. Control interface 34 and source/detector module 54 are operatively linked via an emission signal pathway 56a and two detection signal pathways 56b and 56c. Signal pathways 56a-56c may take the form of optical fibers for transmitting signals in the form of electromagnetic radiation. In a non-limiting example, the fibers can be provided within (interiorly to) the walls of patient circuit 26 so as not to create additional connections (e.g., wires, tubing, fibers, etc.) between gas delivery system 12 and patient interface assembly 28. Alternatively, signal pathways 56a-56c may be bound, or bundled, externally to patient circuit 26. In another non-limiting embodiment, the signal pathways 56a-56c are embedded in the material of the walls forming patient circuit 26. In another embodiment, the signal pathways 56a-56c do not employ fibers and are wireless.

Source/detector module 54 includes a source 58. In the embodiment illustrated in FIG. 7, source 58 is a radiation source, such as a light emitting diode (LED). In other embodiments, source 58 may include any other source for emitting radiation, such as electromagnetic, sonic, ultrasonic, or other radiation. Source 58 is controlled by controller 32 to provide radiation for transmission to control interface 34 via emission signal pathway 56a. For example, controller 32 may control pulse rate, a modulation, a frequency, or other aspects of the radiation. In one embodiment, source/detector module 54 and control interface 34 form a modular system separate from gas delivery system 12 that may be linked to controller 32 in order to retrofit gas delivery system 12 with a control interface that enhances an ease of use for the patient or another individual. In another embodiment, source/detector module 54 is provided integrally in a common housing with gas delivery system at the time of manufacture.

As is shown in FIG. 7, the radiation provided by source 58 along emission signal pathway 56a is received at control interface 34, and is divided by a signal splitter 60, and the resulting radiation beams are guided incident along detection signal paths 56b and 56c. Signal splitter 60 may include any optical component(s) for suitably splitting the radiation from source 58 into a plurality of radiation beams. For example, signal splitter 60 may include polarizing beam splitters, dichroic beam splitters, half mirrors, or other optical splitters. Detection signal paths 56b and 56c then return the radiation beams to source/detector module 54, where they are incident on detectors 62a and 62b, which are operatively linked to controller 32. Detectors 62a and 62b include any radiation detectors suitable for detecting electromagnetic radiation in the frequency range of the radiation generated by source 58. Each of detectors 62a and 62b provides an electrical signal to controller 32 that indicates whether radiation is incident along its associated signal path. Based on the electrical signals received, controller 32 may adjust one or more aspects of the operation of patient treatment system 10.

As is illustrated in FIG. 7, detection signal paths 56b and 56c include one or more switches 64a and 64b, provided at control interface 34, that can be selectively opened and closed by the patient, thereby enabling the patient to selectively open and close detection signal paths 56b and 56c, respectively. Whether the switches 64a and 64b are opened or closed is detected by detectors 62a and 62b, and transmitted to controller 32 via the electrical signals communicated from detectors 62a and 62b to controller 32. Controller 32, in turn, controls the various aspects of patient treatment system 10 (as noted above) in accordance with the selections made by the patient in opening and closing switches 64a and 64b. For example, the patient may control a ramp setting, a pressure relief setting, a humidifier setting, a temperature setting, an oxygen concentration level setting, an on/off control, or other settings or controls.

It will be appreciated that although the embodiment of control interface 34 and source/detector module 54 illustrated provide only two switches at control interface 34, the present invention contemplates alternate embodiments in which more (or fewer) switches are provided to the patient at control interface 34 to enable the patient to control more aspects of patient treatment system 10. In these embodiments, control interface 34 may include a plurality of signal splitters to increase the number of detection signal paths. The increased number of detection signals may be received by a correspondingly increased number of detectors at source/detector module 54.

Figure 8:
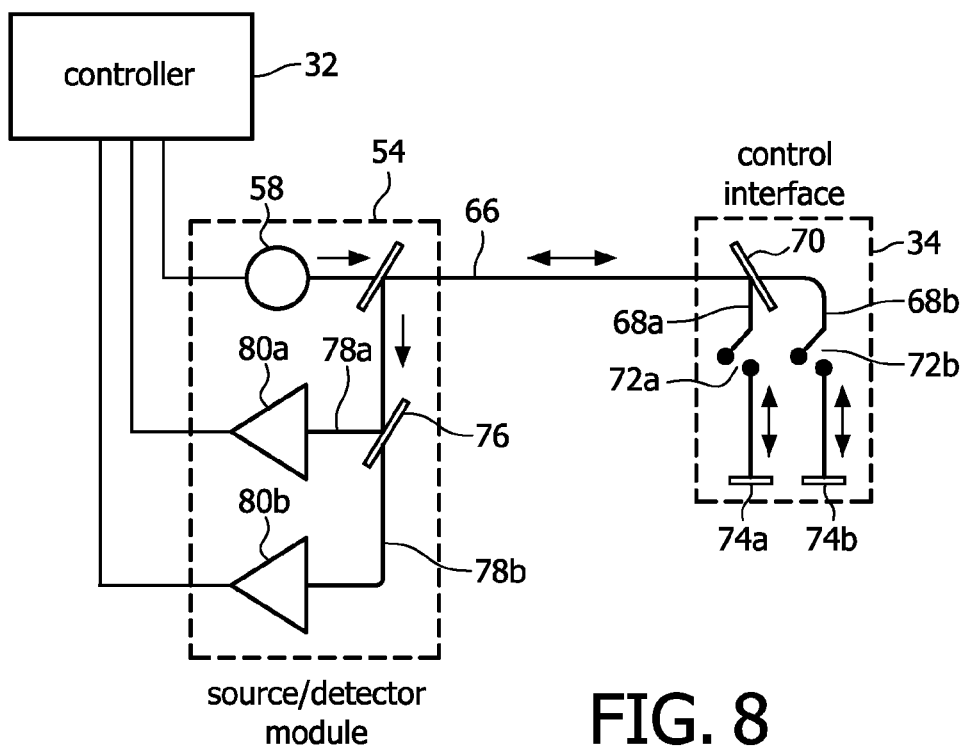
FIG. 8 is a schematic representation of an alternative of the control interface, in accordance with an embodiment of the invention.

FIG. 8 illustrates an alternative configuration of controller 32, in accordance with another embodiment of the invention. In the embodiment shown, radiation from source 58 included in source detector module 54 is transmitted to control interface 34 along a primary signal pathway 66. At control interface 34, the radiation from source 58 is divided into two switched signal pathway 68a and 68b by a dichroic beam splitter 70. The use of dichroic beam splitter 70 ensures that the radiation provided along each of switched signal pathways 68a and 68b will primarily include radiation within a range of frequencies specific to that signal pathway. Each of switched signal pathways 68a and 68b is selectively opened and closed by the patient at control interface 34 via switches 72a and 72b, respectively. The radiation provided along the switched signal pathways 68a and 68b, provided switches 72a and 72b are closed, is reflected by reflective elements 74a and 74b, and returned back along the switched signal pathways 68a and 68b to the dichroic beam splitter 70, which functions to recombine the radiation from the signal pathways 68a and 68b, and direct the combined radiation back toward source/detector module 54 along primary signal pathway 66.

At source/detector module 54, dichroic beam splitter 76 divides the combined radiation along two detection signal pathways 78a and 78b. More specifically, the dichroic beam splitter 76 divides the combined radiation such that the radiation provided along detection signal pathways 78a and 78b include radiation within ranges of frequencies that correspond to the ranges of frequencies of the radiation provided to switched signal pathways 68a and 68b. The radiation provided along detection signal pathways 78a and 78b is then directed incident onto detectors 80a and 80b, which are operatively linked to controller 32. Each of detectors 80a and 80b provide an electrical signal to controller 32 that indicates whether radiation is incident along its associated signal path. As will be appreciated, the electrical signals represent which ones of switches 72a and 72b have been selectively opened or closed by the patient, and controller 32 adjusts the aforementioned various aspects of the operation of patient treatment system 10 based on these selections.

As was described above with respect to the embodiment of FIG. 7, although the embodiment of control interface 34 and source/detector module 54 illustrated in FIG. 8 provide only two switches at control interface 34, the present invention contemplates alternate embodiments in which more (or fewer) switches are provided to the patient at control interface 34 to enable the patient to control more aspects of patient treatment system 10. In these embodiments, control interface 34 may include a plurality of dichroic beam splitters to increase the number of switched signal paths that receive beams of radiation within defined spectral ranges. The increased number of beams of radiation may then be transmitted back to source/detector module 54 via the primary signal pathway 66, and may be received by a correspondingly increased number of detectors.

Figure 9A:
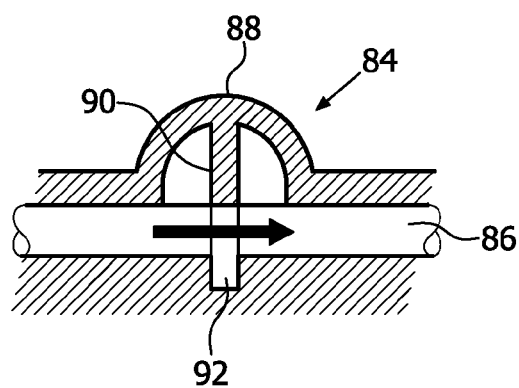
FIGS. 9A and 9B illustrate a switch according to an embodiment of the invention.
Figure 9B:
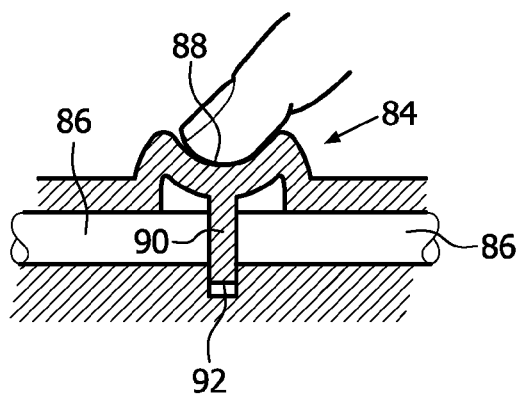

FIGS. 9A and 9B are exemplary illustrations of a switch 84 associated with a signal pathway 86, in accordance with one embodiment of the invention. Switch 84 may be implemented as some or all of switches 64a, 64b, 72a, and 72b of control interface 34 as illustrated in FIGS. 7 and 8, while signal pathway 86 may be implemented as some or all of signal pathways 56b, 56c, 68a, and 68b. Switch 84 includes a depressible surface 88 that is raised with respect to the surface of the surrounding area. Depressible surface 88 is attached to, or formed integrally with, a signal blocking member 90. A channel 92 is provided within signal pathway 86 at switch 84. Signal blocking member 90 can be selectively positioned into channel 92 to block signal pathway 86. The default position of switch 84, illustrated in FIG. 9A, is open, enabling a signal, such as a beam of radiation, to pass through switch 84 along signal pathway 86. In order to close switch 84, as shown in FIG. 9B, the patient applies a force to depressible surface 88, deforming depressible surface 88 and positioning signal blocking member 90 within channel 92 to block a signal, such as a beam of radiation, traveling along signal pathway 86. Other embodiments that employ only passive components at control interface 34 may implement other types of remotely generated signals. For example, a pneumatic system may be implemented in which pressurized gas is diverted from gas delivery system 12, and is directed along signal paths similar to signal pathway 56a-56c illustrated in FIG. 7. In such an embodiment, detectors 62a and 62b would include flow detectors capable of detecting air movement along signal pathways 56b and 56c.

As noted previously, in one embodiment of the invention, depressible surface 88 is raised from the surface of the surrounding area. The depressible surface 88 may be shaped to provide a tactile indication as to the functionality of the associated switch. As a non-limiting example, if switch 84 enables control of a humidifier function, depressible surface 88 may be formed in the shape of a water droplet. Further, in one embodiment of the invention, the radiation emitted by source 58 is in the visible spectrum, and depressible surface 88 is formed from a transparent material so that the radiation passing along signal pathway 86 will illuminate switch 84. This may enhance the ease of use for the patient, since patient treatment system 10 is often employed in a dark room.

Figure 10:
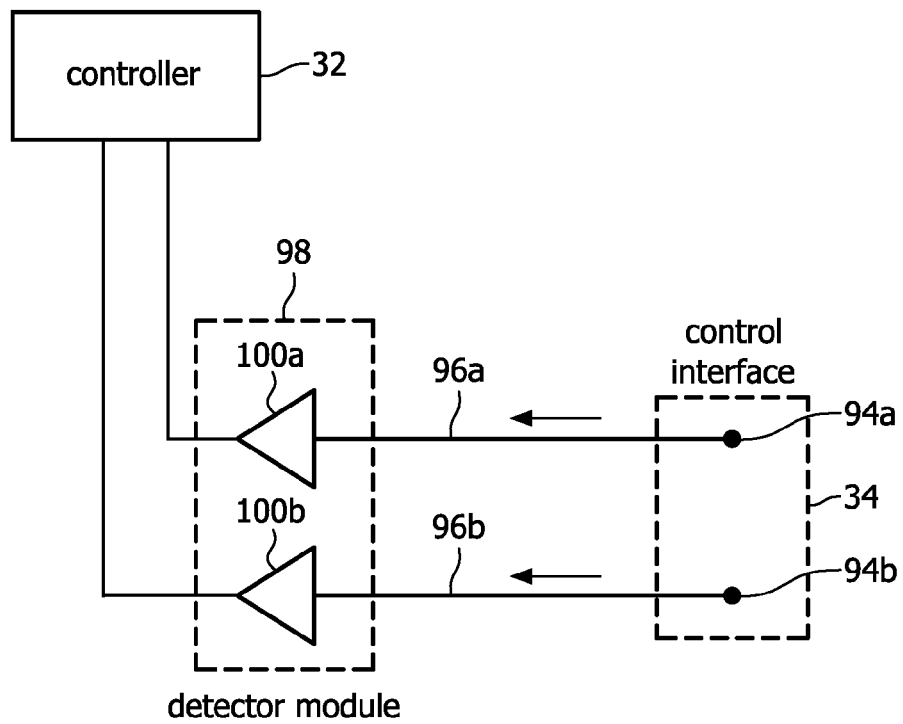
FIG. 10 is a schematic representation of an alternative configuration of the control interface, in accordance with an embodiment of the invention.

FIG. 10 illustrates an embodiment of the invention in which a passive signal is generated remotely from controller 32 of gas delivery system 12. In the embodiment shown, control interface 34 includes a plurality of pneumatic signal sources 94a and 94b. By interacting with the sources 94a and/or 94b, the patient, or another individual, generates pneumatic signals that are directed along signal pathways 96a and/or 96b toward detector module 98. At detector module 98, pneumatic signals within signal pathways 96a and 96b are detected by detectors 100a and 100b. Detectors 100a and 100b may include any device, such as flow detectors, capable of generating a signal representative of the pneumatic signals within signal pathways 96a and 96b. Detectors 100a and 100b are operatively linked with controller 32, and based on the signals generated by detectors 100a and 100b, controller 32 adjusts the operation of patient treatment system 10.

FIGS. 11A and 11B are exemplary illustrations of a pneumatic or hydraulic signal source 102 associated with a signal pathway 104. Source 102 may be implemented as sources 94a and 94b of control interface 34 as illustrated in FIG. 10, while signal pathway 104 may be implemented as signal pathways 96a and 96b. Source 102 includes a depressible surface 106 that is raised with respect to the surface of the surrounding area. A fluid reservoir 108 is defined in part by depressible surface 106, and communicates with signal pathway 104. In order to generate a pneumatic signal, the patient, or another individual, applies a force to depressible surface 106, as shown in FIG. 11B, which causes the collapse of fluid reservoir 108. As fluid reservoir 108 collapses, fluid (e.g., breathable gas, atmospheric gas, liquid, etc.) is forced out of fluid reservoir 108, generating a pulse of fluid along signal pathway 104. The pulse of fluid along signal pathway 104 may then be detected by a suitable detector, and based on this detection, an aspect of the operation of patient treatment system 10 may be adjusted.

FIG. 12 is an exemplary illustration of another embodiment of the invention. In this embodiment, the patient interface assembly 28 carries with it the control interface 34, a power source 110, and a wireless transmitter 112. Based on input from the patient at control interface 34, a wireless signal is transmitted from transmitter 112 to a receiver 114 associated with gas delivery system 12. Receiver 114 is operatively linked to controller 32, which adjusts one or more aspects of the operation of patient treatment system 10 based on the wireless signal. Power source 110 provides the power necessary to operate control interface 34 and transmitter 112. In one embodiment, power source 110 includes a small battery located at patient interface assembly 28. In one embodiment, power source 110 may be replaced with a wired power connection between, for example, gas delivery system 12 and control interface 34. In another embodiment, control interface 34, power source 110, and transmitter 112 are not carried on patient interface assembly 28, but instead are carried or located in another location that is convenient to the patient or another individual. In one embodiment, receiver 114 is capable of being connected to controller 32 of a pre-existing gas delivery system 12, and control interface 34, power source 110, transmitter 112, and receiver 114 provide a mechanism for retrofitting a patient delivery system 10 with a remote control function that is provided to patient delivery system 10 to enhance an ease of use.

It should be apparent that although FIGS. 7, 8, and 10 illustrate particular embodiments of an operative communications link between control interface 34 and gas delivery system 12, control interface 34 may communicate with gas delivery system 12 via any conventional communications link or links. For example, control interface 34 may communicate with gas delivery system 12 via a wired link, a wireless link, a link that transmits an electronic signal, a link that transmits a non-electronic signal, an optical link, an RF link, a microwave link, or other communication links. In one embodiment, control interface 34 is connected with controller 32 of gas delivery system 10 by way of a conventional wired connection, and manipulation of the control interface 34 by the patient, or another individual, to adjust one or more aspects of the operation of patient treatment system 10 results in the transmission of electronic signals to controller 32 that enable the controller to adjust the one or more aspects of the operation of patient treatment system 10 in accordance with the desires of the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface assembly for communicating pressurized gas from a gas delivery system to a patient, the patient interface assembly comprising:
    a patient interface appliance that is physically separate and discrete from the gas delivery system;
    a proximate portion of a patient circuit that delivers pressurized gas from the gas delivery system to the patient interface appliance;
    a headgear assembly that is physically separate and discrete from the gas delivery system, the head gear assembly being configured to mount the patient interface appliance on a user; and
    a control interface configured to provide a control signal to the gas delivery system that adjusts one or more of a humidifier control, a pressure relief control, a ramp control, or an oxygen concentration level control, the control interface being provided on a leash associated with the headgear assembly and comprising a manually actuatable element provided on an exposed surface, wherein the control signal is provided by the control interface responsive to manual manipulation of the manually actuatable element.

2. The system of claim 1, wherein the control interface enables the patient to adjust one or more of a humidifier control, a pressure relief control, or a ramp control via a wireless signal.

3. The system of claim 2, further comprising a wireless transmitter carried by the patient interface assembly that generates a wireless output signal that adjusts one or more of a humidifier control, a pressure relief control, or a ramp control.

4. The system of claim 3, further comprising a power source carried by the patient interface assembly and supplying power to the transmitter.

5. The system of claim 1, wherein the patient interface assembly includes a mask, and wherein the control interface is provided on the mask.

6. The system of claim 1, wherein the patient interface assembly includes a mask and a headgear assembly for mounting the mask on the patient.

7. The system of claim 6, wherein the control interface is provided on the headgear assembly.

8. The system of claim 6, wherein a patient circuit communicates the gas delivery system with the mask, and wherein the patient interface assembly includes a proximate portion of the patient circuit.

9. The system of claim 1, wherein the patient interface assembly includes a proximate portion of a patient circuit that communicates the gas delivery system with the patient interface assembly.

10. The system of claim 1, further comprising a gas source operatively connected to the gas delivery system in order to supply the breathable gas to the gas delivery system.

11. The system of claim 1, wherein the gas delivery system incorporates a gas supply.

12. The patient interface assembly of claim 1, wherein the leash is removably secured to the headgear assembly at one side.

13. The patient interface assembly of claim 1, wherein the control interface provides the control signal by passively interacting with a non-electronic signal generated remotely from the control interface.

14. The patient interface assembly of claim 13, wherein the non-electronic signal includes at least one of an optical signal or a pneumatic signal.

15. The patient interface assembly of claim 13, wherein the non-electronic signal is generated at the gas delivery system.

16. The system of claim 15, wherein a patient circuit communicates the gas delivery system with the patient interface, and wherein the non-electronic signal is carried to the control interface and/or to the gas delivery system via a signal pathway integrally formed with a patient circuit.

17. The patient interface assembly of claim 1, wherein the control signal adjusts a control that is also adjustable via an input module disposed on the gas delivery system.

18. The patient treatment system of claim 17, wherein the at least one aspect of the patient treatment system controlled via the input module and the controls adjustable via the control interface comprise a common aspect that is controllable via both of the input module and the control interface.

* * * * *